US00PP35738P2

(12) United States Plant Patent
Kievit

(10) Patent No.: US PP35,738 P2
(45) Date of Patent: Apr. 9, 2024

(54) ***STACHYS* PLANT NAMED 'BALSTACLAMB'**

(50) Latin Name: *Stachys byzantina*
Varietal Denomination: Balstaclamb

(71) Applicant: Ball Horticultural Company, West Chicago, IL (US)

(72) Inventor: Christa Kievit, Hem (NL)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 18/368,464

(22) Filed: Sep. 14, 2023

(51) Int. Cl.
*A01H 6/00* (2018.01)
*A01H 5/02* (2018.01)

(52) U.S. Cl.
USPC ..... Plt./263.1

(58) Field of Classification Search
USPC ..... Plt./263.1
CPC ..... A01H 6/00; A01H 5/02
See application file for complete search history.

*Primary Examiner* — Keith O. Robinson
(74) *Attorney, Agent, or Firm* — Audrey Charles

(57) ABSTRACT

A new and distinct cultivar of *Stachys* plant named 'Balstaclamb', characterized by its light purple-colored flowers, light grey-green, silvery colored foliage, and moderately vigorous, spreading growth habit, is disclosed.

1 Drawing Sheet

Latin name of genus and species of plant claimed: *Stachys byzantina.*

Variety denomination: 'Balstaclamb'.

BACKGROUND OF THE INVENTION

The present invention relates to a new and distinct cultivar of *Stachys* plant botanically known as *Stachys byzantina* and hereinafter referred to by the cultivar name 'Balstaclamb'.

The new cultivar originated in a controlled breeding program Hem, The Netherlands during the summer of 2017. The objective of the breeding program was the development of *Stachys* cultivars having shorter inflorescences and decorative foliage suitable for ground cover use.

The new *Stachys* cultivar is the result of a self-pollination of the proprietary *Stachys byzantina* breeding selection coded A23, not patented, characterized by its light purple-colored flowers, light grey-green, silvery colored foliage, and vigorous, spreading growth habit. The new cultivar was discovered and selected as a single flowering plant within the progeny of the above stated self-pollination during June 2018 in a controlled environment in Hem, The Netherlands.

Asexual reproduction of the new cultivar by terminal stem cuttings since June 2018 in Hem, The Netherlands and Elburn, Illinois has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balstaclamb' as a new and distinct cultivar of *Stachys* plant:

1. Light purple-colored flowers;
2. Light grey-green, silvery colored foliage; and
3. Moderately vigorous, spreading growth habit.

Plants of the new cultivar differ from plants of the parent primarily in having smaller sized leaves, reduced growth vigor, and higher density leaf pubescence.

Of the many commercially available *Stachys* cultivars, the most similar in comparison to the new cultivar is 'Silver Carpet', not patented. However, in side-by-side comparisons, plants of the new cultivar differ from plants of 'Silver Carpet' in at least the following characteristics:

1. Plants of the new cultivar have shorter inflorescences than plants of 'Silver Carpet'; and
2. Plants of the new cultivar have smaller sized leaves than plants of 'Silver Carpet'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Balstaclamb'. The plants were approximately 4.5 months old and grown in 2.5-quart containers for approximately seven weeks in an outdoor nursery environment in West Chicago, Illinois. Plants were given two pinches, one at approximately two weeks before transplant and one at approximately four weeks after transplant. The inflorescence figure was taken from 1.5 year old plants transplanted to the field the previous fall season.

DETAILED BOTANICAL DESCRIPTION

Figure 1:
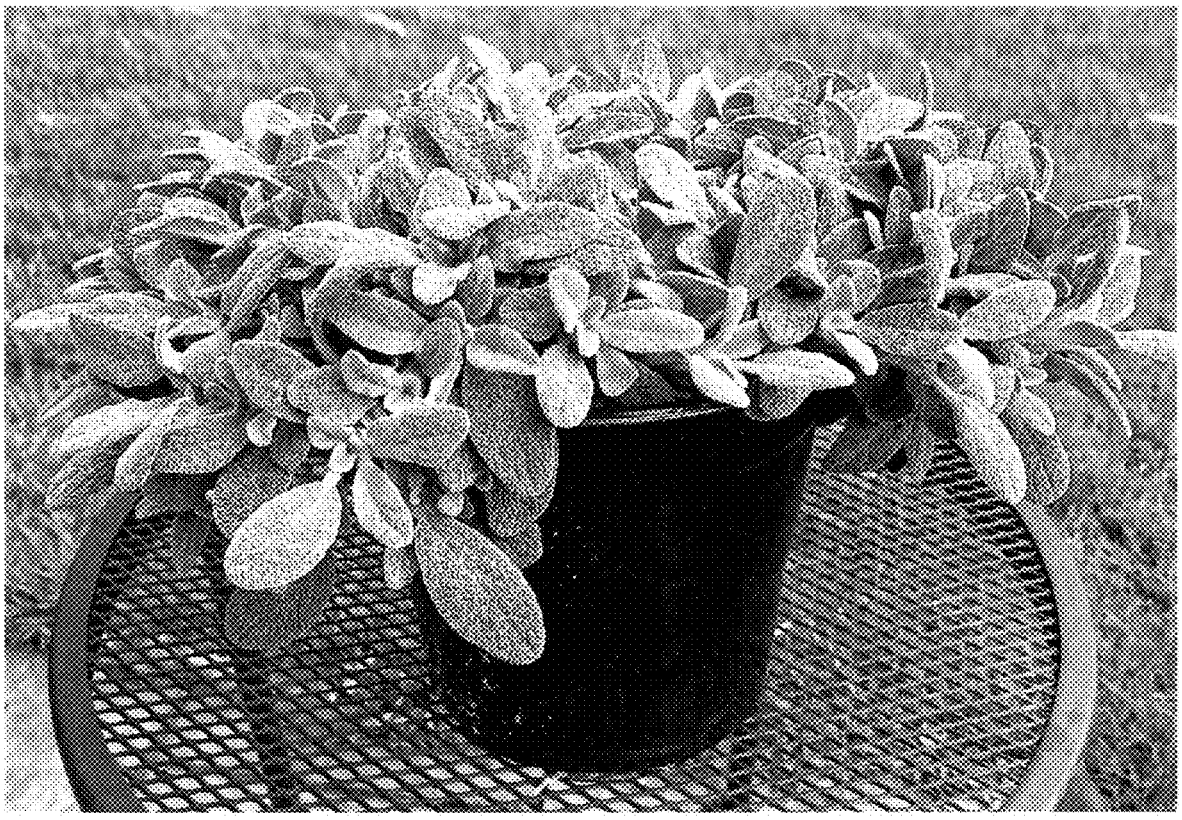
FIG. 1 illustrates a side view of the overall growth and flowering habit of 'Balstaclamb'.
Figure 2:
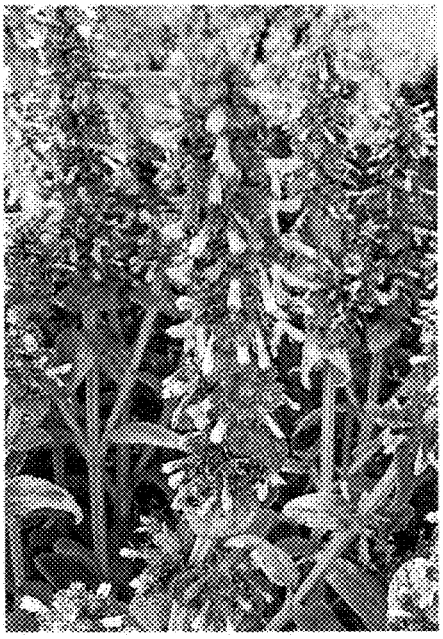
FIG. 2 illustrates a close-up view of an individual inflorescence of 'Balstaclamb'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in June 2023 under natural light conditions in Naperville, Illinois.

The following descriptions and measurements describe approximately 4.5-month old plants produced from cuttings from stock plants and grown under conditions comparable to those used in commercial practice. Approximately seven weeks after sticking, rooted plants were transplanted into 2.5-quart containers utilizing a soilless growth medium and grown for five weeks. Plants were then transferred to an outdoor nursery environment in West Chicago, Illinois and grown for approximately seven weeks. Plants were given two pinches, one at approximately two weeks before transplant and one at approximately four weeks after transplant. Prior to transferring outdoors, plants were grown in a polycarbonate greenhouse in West Chicago, Illinois. Greenhouse temperatures were maintained at approximately 70° F. to 75° F. (21.1° C. to 23.9° C.) during the day and approximately 60° F. to 65° F. (15.6° C. to 18.3° C.) during the night. Supplemental lighting was used. The inflorescence data was taken from 1.5 year old plants transplanted to the field the previous fall season. Measurements and numerical values represent averages of typical plants.

Botanical classification: *Stachys byzantina* 'Balstaclamb'.

Parentage:

*Female and male parent.*—Proprietary *Stachys byzantina* breeding selection coded A23, not patented.

Propagation:

*Type cutting.*—Terminal stem.

*Time to initiate roots.*—Approximately 6 to 7 days.

*Time to produce a rooted cutting.*—Approximately 5 to 6 weeks.

*Root description.*—Fine to medium, fibrous, dense.

*Rooting habit.*—Freely branching.

Plant description:

*Commercial crop time.*—Approximately 6 to 8 weeks from a rooted cutting to finish in a 15 cm container.

*Growth habit and general appearance.*—Herbaceous perennial, moderately vigorous, spreading.

*Hardiness.*—USDA Zone 4a (−30° F. to −25° F./−34.4° C. to −31.7° C.).

*Size.*—Height: Approximately 7.0 cm. Width: Approximately 35.0 cm.

*Branching habit.*—Freely branching, dense. Quantity of main branches per plant: Approximately 8 main branches, with laterals potentially at every node.

*Branch.*—Shape: Square in cross section. Strength: Strong. Length: Approximately 7.5 cm. Diameter: Approximately 3.0 mm to 7.0 mm. Length of central internode: Approximately 1.2 cm. Texture: Lanate. Pubescence color: NN155D. Color of young stems: 145C, appearing lighter 145D due to pubescence. Color of mature stems: 145C, appearing lighter 145D due to pubescence, becoming woody N199B at base of plant with age.

Foliage description:

*General description.*—Quantity of leaves per main branch: Approximately 8. Fragrance: None detected. Form: Simple. Arrangement: Opposite, decurrent.

*Leaves.*—Aspect: Primarily acute angle to stem with tips downward turning with age. Shape: Elliptic. Margin: Crenate. Apex: Rounded. Base: Rounded. Venation pattern: Pinnate. Length of mature leaf: Approximately 4.0 cm. Width of mature leaf: Approximately 2.2 cm. Texture of upper surface: Lanate, moderately rugose. Texture of lower surface: Lanate, cancellate. Pubescence color: NN155D. Color of upper surface of young foliage: 137A with indistinguishable venation, appears 191B due to pubescence. Color of lower surface of young foliage: 138B with venation of 145D, appear slightly lighter due to pubescence. Color of upper surface of mature foliage: 137A with indistinguishable venation, appears 191A due to pubescence. Color of lower surface of mature foliage: 138B with venation of 145D, appear slightly lighter due to pubescence.

*Petiole.*—Length: Approximately 3.0 cm. Diameter: Approximately 5.0 mm at base. Texture: Lanate. Pubescence color: NN155D. Color: 145C, appearing lighter 145D due to pubescence.

Flowering description:

*Flowering habit.*—'Balstaclamb' is freely flowering under outdoor growing conditions with substantially continuous blooming in the summer months.

Inflorescence description:

*General description.*—Type: Terminal raceme. Quantity per plant: Approximately 48. Fragrance: Slight. Length: Approximately 5.0 cm. Width: Approximately 2.5 cm to 3.5 cm. Quantity of fully open flowers per inflorescence: Approximately 100.

*Peduncles.*—Shape: Square in cross section. Strength: Strong, rigid. Aspect: Erect. Length: Approximately 14.0 cm. Diameter: Approximately 5.0 mm. Texture: Lanate. Pubescence color: NN155D. Color: 146B, appearing 191C due to pubescence.

Flower description:

*Type.*—Solitary, labiate, zygomorphic, sessile. Aspect: Facing outward.

*Flower buds.*—Shape: Obovoid. Length: Approximately 6.0 mm. Diameter: Approximately 4.0 mm. Texture: Densely pubescent. Texture: Lanate. Pubescence color: NN155D. Color: 146B, appearing 191C due to pubescence.

*Corolla.*—Shape: Bilabiate, 5 petals consisting of an upper lip with 2 lobes and a lower lip with 3 lobes, consisting of 2 lateral lobes and one central lobes. Length: Approximately 8.0 mm. Width: Approximately 4.0 mm. Depth: Approximately 1.4 cm.

*Upper lip lobes.*—Shape: Obovate. Margin: Entire. Apex: Emarginate. Length from throat: Approximately 5.0 mm. Width: Approximately 2.0 mm. Texture of inner surface: Glabrous. Texture of outer surface: Lanate. Pubescence color: NN155D. Color of inner surface when fully open: 76A to 76B. Color of outer surface when fully open: 76B to 76C to slightly lighter due to pubescence.

*Lower lip lobes.*—Shape of lateral lobes: Oblong. Shape of central lobe: Obovate. Margins: Entire. Apex of lateral lobes: Obtuse. Apex of central lobe: Emarginate. Length of lateral lobes from throat: Approximately 4.0 mm. Width of lateral lobes: Approximately 1.5 mm. Length of central lobe from throat: Approximately 6.0 mm. Width of central lobe: Approximately 3.0 mm. Texture of inner surface: Glabrous. Texture of outer surface: Lanate. Pubescence color: NN155D. Color of inner surface when fully open: 76A to 76B. Color of outer surface when fully open: 76B to 76C to slightly lighter due to pubescence.

*Corolla tube.*—Length: Approximately 9.0 mm. Diameter: Approximately: 4.0 mm. Texture of inner and outer surfaces: Glabrous. Color of inner and outer surfaces: NN155D.

*Calyx.*—Shape: Cupped. Length: Approximately 7.0 mm. Diameter: Approximately 4.0 mm.

*Sepals.*—Quantity per flower: 5, fused with five tips. Apex: Acuminate. Length: Approximately 7.0 mm. Width: Approximately 1.5 mm. Texture of inner surface: Glabrous. Texture of outer surface: Lanate. Pubescence color: NN155D. Color of inner surface: 146C. Color of lower (outer) surface: 146C appearing lighter due to pubescence, tips of 77A.

*Reproductive organs.*—Androecium: Stamen quantity: 4 per flower, filaments adnate to corolla tube. Filament length of free portion: Approximately 3.0 mm. Filament color: NN155D tinted with 76A. Anther shape: Ellipsoid. Anther length: Approximately 1.0 mm. Anther color: NN155A. Pollen amount: Moderate. Pollen color: NN155D. Gynoecium: Pistil quantity: 1 per flower. Pistil length: Approximately 1.4 cm. Stigma shape: Bifid. Stigma branch length: Less than 1.0 mm. Stigma color: 76D. Style length: Approximately 1.3 cm. Style color: NN155D tinted with 76D. Ovary length: Approximately 1.0 mm. Ovary color: 155A.

Seed and fruit production: Neither seed nor fruit production has been observed.

Disease and pest resistance: Resistance to pathogens and pests common to *Stachys* has not been observed.

What is claimed is:

1. A new and distinct cultivar of *Stachys* plant named 'Balstaclamb', substantially as herein illustrated and described.

* * * * *